United States Patent [19]

Bethge et al.

[11] Patent Number: 5,705,192

[45] Date of Patent: Jan. 6, 1998

[54] METHOD OF PRODUCING FLOWABLE R,S-THIOCTIC ACID, R,S-THIOCTIC ACID AND ITS USE

[75] Inventors: Horst Bethge, Rodenbach; Kurt Klostermann, Sulzbach-Soden; Roland Möller, Hammersbach; Gerhard Sator, Dieburg, all of Germany

[73] Assignee: ASTA Medica Aktiengesellschaft, Dresden, Germany

[21] Appl. No.: 618,790

[22] Filed: Mar. 20, 1996

[30] Foreign Application Priority Data

Mar. 21, 1995 [DE] Germany ............... 195 10 130.8

[51] Int. Cl.$^6$ ............... A61K 9/20; A61K 9/14; C07D 339/04
[52] U.S. Cl. ............... 424/489; 424/464; 549/39
[58] Field of Search ............... 549/39; 424/464, 424/489

[56] References Cited

U.S. PATENT DOCUMENTS

| | | | |
|---|---|---|---|
| 5,376,382 | 12/1994 | Goedle et al. | 424/464 |
| 5,455,264 | 10/1995 | Beisswenger et al. | 514/440 |
| 5,527,539 | 6/1996 | Sarlikiotis et al. | 424/464 |

*Primary Examiner*—Deborah Lambkin
*Attorney, Agent, or Firm*—Cushman Darby & Cushman, IP Group of Pillsbury Madison & Sutro LLP

[57] ABSTRACT

1. A method of producing flowable R,S-thioctic acid, R,S-thioctic acid and its use.

2.1. Known methods of preparing flowable thioctic acid which can be galenically further processed by pressing to highly-concentrated, solid presentations with active-substance contents of more than 200 mg pure substance require the mixing of the thioctic-acid forms of different origins and/or a spraying on of galenic adjuvants from aqueous solution and a subsequent grinding process in order to arrive at a pressable granulate.

2.2. As a result of the fact that thioctic acid of any origin is placed in the fluid bed of a device suited for producing a fluid bed and that a built-up granulate consisting of thioctic acid is obtained by spraying a solution of thioctic acid of any origin onto the matter placed in the fluid bed under simultaneous removal of the solvent, it is possible to make a thioctic-acid form available which does not adhere to the pressing tool or exhibit a tendency to form fissures on the tablet even when tablets with 600 mg or more active-substance content are prepared. The novel R,S-thioctic acid has a specific surface of $>0.7$ m$^2$/g and a number of mesopores with a diameter between 2 and 30 nm.

19 Claims, No Drawings

METHOD OF PRODUCING FLOWABLE R,S-THIOCTIC ACID, R,S-THIOCTIC ACID AND ITS USE

BACKGROUND OF THE INVENTION

1. Field of the Invention

The invention is relative to a method of producing flowable R,S-thioctic acid which can be further processed galenically by pressing to highly concentrated, solid presentations with active-substance contents of more than 200 mg pure substance. In particular, the invention also permits a simple preparation of high-dose tablets with 600 mg or more of pure-substance content.

2. Background Information

R,S-thioctic acid (D,L-alpha-lipoic acid) is used in pharmaceutical formulations both in infusion solutions and also as a solid, galenic formulation for oral use. When thioctic acid is mentioned in the following it always signifies both the enantiomerically pure compounds (R- or S-thioctic acid) as well as the racemic mixture (R,S-thioctic acid) and mixtures with any desired enantiomer contents.

As a rule, synthetically obtained D,L thioctic acid obtained via the precursor of dihydrolipoic acid (6,8-dimercaptooctanoic acid) by oxidation is employed for pharmaceutical use. The synthetic method can also be carried out in such a manner here that enantiomerically pure R- or S-thioctic acid (D- or L-alpha-lipoic acid) is produced from enantiomerically pure R- or S-dihydrolipoic acid (DE 41 37 733, EP 0,427,247). Enantiomerically pure R-thioctic acid or S-thioctic acid is also accessible according to the method described in DE-OS 36 29 116 and can be used in an especially advantageous manner.

Methods of producing thioctic-acid forms which are known in the literature comprise, among others, methods (Chem. Ber. 1959, 1177) in which the dimercaptooctanoic acid is distilled and purified after oxidation to thioctic acid again by distillation in order to finally be obtained in crystalline form at −70° C. from ethyl acetate.

A further method (J. Am. Chem. Soc. 77 (1955), 416) uses the viscous oil obtainable after the oxidation of dimercaptooctanoic acid by evaporating the organic solvent to low bulk. The latter is multiply extracted with Skellysolve B, during which a changing amount of a "polymeric" material remains. The combined extracts are seeded and crystallized at room temperature or for a few hours in a refrigerator. The recrystallization from Skellysolve B finally yields a reagent-grade product with a melting point of 61° C.–62° C.

A further formula (J. Am. Chem. Soc. 77 (1955) 5148) recommends cyclohexane for extraction and crystallization, which also yielded enantiomerically pure (+)-alpha-lipoic acid using an analogous [analog]approach (J. Chem. Soc. Perkin Trans. 1 (1990), 1615).

A method (DE 42 35 912) using organic solvent with a relative permittivity ε of 2.5 to 5.5 for the extraction and crystallization is finding industrial application today.

However, the product previously commercially available is present in a form which is not very favorable for being further processed galenically to solid presentations (lacking flowability, unfavorable grain-size distribution).

The previously obtainable thioctic-acid forms exhibit quite poor properties in particular in the production of highly-concentrated tablets by pressing. This problem was able to be combatted in the past only by mixing different, commercially available thioctic-acid forms in order to set a certain grain-size distribution and a subsequent, intensive granulation. Thus, the practical state of the art is to produce a mixture of approximately 40 parts by weight thioctic acid, obtained by recrystallization e.g. according to DE-OS 42 35 912, with 60 parts by weight thioctic acid, which was probably purified by a distillation-and/or melting process and by breaking [milling, crushing] the melt, and to press this mixture under the addition of approximately 15% by weight adjuvants, relative to 100% by weight thioctic acid, to corresponding, solid presentations. It is also known in this connection that the 60:40 mixture can be placed in a fluid bed of a suitable device, the adjuvants sprayed out of an aqueous solution onto the placed mixture and the product obtained ground to a pressable granulate.

This method used today in practice has several notable disadvantages. The mixing of "different", commercially available thioctic-acid charges does not result in the desired success in any combination but rather only in quite specific ones, e.g. those cited above. Moreover, even a "tested" ["proven"] mixture of thioctic acids of various origins frequently poses problems in that high-dosage, solid presentations, that is, e.g. tablets with 600 mg thioctic-acid content or more, can not be produced in the required quality, even if the known requirements are observed. Then there is the aggravating circumstance that it has been well-known up to the present that the grain-size spectrum of the thioctic-acid mixture constitutes a very important variable for the pressing; on the other hand, however, it has not been possible up to the present to exactly specify the requirements, as regards the grain-size spectrum, for a pressing.

SUMMARY OF THE INVENTION

In view of the state of the art indicated and discussed herein the present invention consequently had the problem of indicating a method of the initially mentioned type which permits the production of a pure, pharmaceutically useable thioctic-acid form which assures an easier galenic further processing for solid presentations and which is in particular suitable for being pressed to highly concentrated presentations without necessarily being mixed with other available thioctic-acid forms.

The invention also had the problem of a novel thioctic-acid form with processing properties which exceed the known thioctic acids, at least as regards the suitability for high-dosage presentations. At the same time, a product with comparatively low residual solvent contents (compared with commercially available thioctic-acid forms) should be able to be produced.

The basic problem of the invention as well as other problems not designated in detail are solved by a method of the initially mentioned type with the features of the characterizing part of claim 1. Advantageous method modifications are indicated in the claims referring to claim 1. As regards product technology, the subject matter of claim 14 constitutes a solution of the problem of the invention whereas preferred embodiments are placed under protection in the dependent substance claims.

As a result of the fact that thioctic acid of any origin is placed in the fluid bed of a device suited for producing a fluid bed and that a built-up [pelletized] granulate consisting of thioctic acid is obtained by spraying a solution of thioctic acid of any origin onto the matter placed in the fluid bed under simultaneous removal of the solvent, it is possible to make a thioctic-acid form available which 1. Is flowable;
2. Can be processed with the use of less than 20% % by weight adjuvants for galenic further processing;

3
3. Can be further processed without having to adjust a processable mixture by mixing two thioctic-acid charges of different origins; and
4. Makes available highly-concentrated, solid preparations with active-substance contents of more than 200 mg pure substance thereby, especially by pressing to tablets.
5. In addition, the product in accordance with the invention displays clearly lower residual solvent contents than previously known thioctic-acid forms.

In the framework of the invention the term R,S-thioctic acid of any origin or any source denotes a product which basically satisfies the requirements resulting from its usage as pharmaceutical product as regards its purity. Accordingly, the R,S-thioctic acids which can be used are not raw products; however, they can comprise a certain amount of impurities stemming e.g. from a purification process such as e.g. a recrystallization from a solvent.

Thus, the only prerequisite for the suitability of thioctic acid for the method of the invention is the volatility of any impurities contained in the thioctic acid under the conditions of pressure and temperature suitable for carrying out the production method of the invention.

Thus, the thioctic acids which are used according to the invention in an advantageous manner as initial [preparatory] matter include, among others, the R,S-thioctic-acid forms obtainable according to the methods in DE-A 42 35 912; J. am. Chem. Soc. 77 (1955), 5148; J. Chem. Soc. Perkin Trans. 1 (1990), 1615; J. Am. Chem. Soc. 77 (1955), 426; Chem. Ber. 1959, 1177; DE-A 36 29 116; EP-A 0,427,247; DE-A 41 37 773 as well as the R,S-thioctic-acid form accessible according to the method itself described herein.

The possibility of producing highly-concentrated, solid presentations from the product accessible in accordance with the method of the invention is especially advantageous. In the invention the term highly concentrated denotes a presentation whose active-component portion is >80% by weight. That is, as a result of the fact that the portion of galenic adjuvants can be held to <20% by weight, high-dosage presentations, e.g. tablets, can be better administered.

Customary adjuvants are familiar to a galenist.

In order to obtain a product in accordance with the invention the thioctic acid is placed in the fluid bed of a device suitable for producing a fluid bed. It is understood that the thioctic acid placed therein forms the fluid bed itself when the invention is carried out. The concept "fluid bed" signifies, in the context of the invention, that gases flow from below through the matter placed in the bed e.g. as fine bulk material resting on perforated bottoms, during which a state arises under certain conditions of flow which resembles that of a boiling liquid. The devices suitable for producing a fluid bed are known to the expert in the art and described e.g. in Winnacker-Kuchler (3.) 7:31–63; Mathur et al. (Adr. Chem. engineer. 9 (1974)); Baerns (Chem. Ing. Techn. 40 (1968) 737–39) or Simon (Chemie-Techn. 5 (1976) 277–80).

According to the invention a solution of thioctic acid of any origin is now sprayed onto the thioctic acid in the fluid bed, that is, in the final analysis, onto the thioctic-acid fluid bed. The spraying-on or spraying [atomizing] of the thioctic-acid solution occurs in the sense of a spray drying, that is, the solvent is removed and the thioctic acid simultaneously applied onto the matter in the fluid bed in the manner of a built-up granulation or a fluid-bed coating process.

Basically, dry or selectively also solvent-moist thioctic acid can be used in the method of the invention as stationary phase, that is, as product placed in the fluid bed. The use of solvent-moist thioctic acid is especially advantageous thereby since an additional drying step can be saved in this manner.

4
The amount of stationary phase in relation to the amount of sprayed-on phase of thioctic acid is not especially critical according to the invention. However, the amount of stationary phase relative to the total amount of product obtained should not be below an amount of about 10% by weight since otherwise the success of the method of the invention could be rendered questionable. Furthermore, it is not especially logical to place amounts greater than 50% by weight of stationary phase in the fluid bed since, with the exception of the instance in which a product resulting from the method of the invention is already used as stationary phase, the amount of the coating of the product might not suffice any longer to assure the advantageous properties of the product of the invention over the complete property spectrum. It has proven to be especially advantageous from practical standpoints if approximately 25% by weight stationary phase of a thioctic acid of any origin is placed ["in the fluid bed" understood] onto which the remaining 75% by weight from the solvent phase is sprayed. This % by weight data regarding the thioctic acid always refers to 100% by weight dry thioctic acid, which dry thioctic acid means the product comprising the sum of the phase placed [in the bed] and of the sprayed-on thioctic acid at the end of the built-up granulation in accordance with the invention.

As already indicated above, the origin of the thioctic acid placed in the fluid bed as matter or as fluid bed is immaterial. Nevertheless, the use of solvent-moist thioctic acid proved to be extremely favorable according to the invention in an especially preferred method variant which thioctic acid originates from a production method in which one part thioctic acid is dissolved at 10° C. to 60° C. in 5–20 parts solvent or solvent mixture and cooled off within 2 to 10 hours to 0° C. to −20° C., which solvent or solvent mixture has a relative permittivity $\epsilon$ between 2.5 and 5.5. This production variant corresponds to the method disclosed in DE-A 42 35 912. The use of the thioctic-acid product obtainable according to this method in the method of the invention results in a product which can be quite excellently pressed into highly-concentrated presentations in the form of tablets.

It has furthermore proved to be advantageous, as already indicated above, if thioctic-acid product resulting from the method of the invention can be reused as initial matter [i.e. matter placed in the bed]. This therefore concerns a typical build-up granulation [pelletizing].

The result of the spraying of a thioctic-acid solution onto initial matter consisting of dry or selectively also solvent-moist thioctic acid in the fluid bed of a suitable fluid-bed dryer can be influenced by the purposeful adjusting of a number of parameters. Thus, parameters such as product temperature in the fluid bed, spray pressure and spray rate, concentration of the solution to be sprayed on as well as the type and quality of the solvent used play a part for the invention.

In an especially preferred method variant of the invention a highly-concentrated solution of thioctic acid is sprayed onto the initial matter with purposeful adjustment of product temperature, spray pressure and spray rate so that the solvent evaporates and thioctic acid crystallizes out.

The fluid bed, that is, the product in the fluid bed, can basically be maintained thereby at any temperature compatible with the thioctic acid. In a preferred embodiment of the method of the invention the spray solution is therefore sprayed into a product fluid bed of 0° to 60° C. A temperature range of 20° to 40° C. for the product fluid bed is especially preferred.

As regards the spray pressure, the method itself is not especially critical. The method of the invention can be carried out under normal pressure, a slight overpressure or also in a vacuum. The method of the invention is therefore characterized in that the spraying is carried out at 100 to 1200 mbar. Especially preferred pressure ranges are located below the normal pressure at a slight vacuum of approximately 600 to 800 mbar. It is especially advantageous for the invention in every instance if the spraying is carried out in such a manner that a spray crystallization arises in the fluid bed. This means that the product in the fluid bed is converted during the method of the invention into a form which is more likely crystalline.

The spray rate itself, that is, therefore, the weight of the solution in grams which is sprayed in the unit of time measured in minutes onto the initial matter in the fluid bed, is a function of various criteria. Thus, the following, among others, are to be taken into consideration: The size and the volume of the apparatus comprising the fluid bed; the progression of the product formation, because an increasing amount of product in the fluid bed allows an increase of the spray rate; finally, the spray rate controls and influences the grain size itself and the distribution of the grain size; in general, a higher spray rate results in a larger grain.

A large number of compounds can be considered as solvent for the solution of thioctic acid to be sprayed on. Thus, the solvent should meet the condition that residual amounts of the solvent should be physiologically tolerable in the method product and, in particular, the residual amount of solvent must be able to be lowered with simple means to the legal limits or below them. Furthermore, the solvent should have the property of receiving and dissolving as great an amount of thioctic acid as possible. Finally, the solvent should be inert to the product, have as low an evaporation enthalpy as possible and have these properties in particular in the temperature range compatible with thioctic acid. The following can serve by way of example as solvent for the invention: Aliphatic hydrocarbons with a carbon chain length between 3 and 10 carbons, cycloaliphatic hydrocarbons such as cyclopentane, cyclohexane, methylcyclohexane, aromatic hydrocarbons which are liquid, aliphatic or cycloaliphatic alcohols with 2 to 6 carbon atoms, esters of aliphatic carboxylic acids with 2 to 6 carbon atoms or cycloaliphatic carboxylic acids with 3 to 6 carbon atoms and aliphatic alcohols with 2 to 6 carbon atoms or cycloaliphatic alcohols with 3 to 6 carbon atoms, aliphatic or cycloaliphatic ketones with 3 to 10 carbon atoms, ethers and glycol ethers or homogeneous mixtures of the named solvents. Especially preferred solvents which splendidly correspond in particular to the above-indicated requirements are, among others, acetone and/or ethyl acetate.

According to the invention the concentration of the spray solution can differ over a broad range. Thus, the concentration of the spray solution in one method variant of the invention is between approximately 10 and 80%. According to the invention the highest possible ranges are striven for, since in this manner the expense and the amount of solvent required for the spray solution can be distinctly and advantageously reduced.

According to the method of the invention a flowable product with a bulk weight between 500 and 900 g/l results in a preferred embodiment which is superbly suited for being galenically further processed to solid presentations and especially for being pressed into highly-concentrated, solid presentations and which has, in particular, a suitable grain-size distribution and particle quality. In addition, in the product in accordance with the invention the residual solvent content in comparison to thioctic acid is distinctly lower than e.g. in the method known from the state of the art in the form of DE-A 42 35 912. The method of the invention is therefore characterized in a preferred variant in that a product with a residual solvent content of organic solvents of a total of <1000 ppm is obtained.

Other subject matter of the invention is constituted by a novel R,S-thioctic acid characterized by a specific surface of >0.7 m$^2$/g and an amount of mesopores with a diameter between 2 and 30 nm.

The specific surface of the R,S-thioctic acid of the invention can be determined by dynamic test methods known to the expert in the art.

In comparison to known R,S-thioctic acids the product of the invention has a distinctly larger specific surface. The specific surface of the R,S-thioctic acid of the invention is preferably in a range of 0.8–1.2 m$^2$/g, especially preferably between 0.84 and 1.05 m$^2$/g.

Moreover, the R,S-thioctic acid of the invention has a number of so-called mesopores. They are pores with a diameter between 2–30 nm which can not be demonstrated in traditional thioctic acids. Micropores with a diameter <2 nm can not be demonstrated in the R,S-thioctic acid of the invention.

In a preferred embodiment the R,S-thioctic acid of the invention is characterized in that the volume of the mesopores with a diameter between 2 and 30 nm per gram R,S-thioctic acid is between 0.001 and 0.005 ml/g.

The pore volumes were determined according to DIN 66 133 (amended as of Oct. 1, 1992).

In addition to the mesopores the thioctic acids of the invention also have so-called macropores. These are pores with a diameter >30 nm.

Their pore volume per g substance is as a rule considerably greater than that of the mesopores.

It is especially favorable if the ratio of the volume of mesopores with a diameter between 2 and 30 nm per gram R,S-thioctic acid to the volume of macropores with a diameter >30 nm per gram R,S-thioctic acid is between 1:1000 and 1:10, preferably between 1:200 and 1:50.

As explained, the grain-size distribution of the product of the invention can be influenced in a purposeful manner by adjusting the parameters such as product temperature, spray pressure, spray rate, quality [nature] of the spray nozzle and by varying the spray-nozzle position. The properties such as adhering to the pressing tool or a tendency to form fissures on the tablet observed in the case of the previously obtainable thioctic-acid forms are not observed in the further processing of the product of the invention to tablets. Therefore, a particularly expensive granulation process can be eliminated in the galenic further processing.

DETAILED DESCRIPTION OF THE INVENTION

The invention is explained further in the following using examples.

EXAMPLE 1

Fluid-bed drying system Glatt company GPCG 1 / Top-spray with supply air/exhaust air; two-component [two-fluid, binary] nozzle d=1.2 mm; nozzle installation "top"; spray pressure: 1.4 bar
Initial product: 250 g thioctic acid (sieved <1250μ)
[lit. "initial matter of the product"]
Spray solution: 750 g thioctic acid, 1125 g ethyl acetate The initial product is heated to 30° C. with the aid of the supply air approximately 40° C. warm and the spraying in of the solution is started at this product temperature. Spray rate:

25 g/min, during which the dosing is gradually raised to 58 g/min. The supply-air temperature is maintained constant at 40° C. The product temperature settles [is adjusted] to 28°–32° C.

After the end of the spraying [in] the matter is allowed to dry 10 min, also at a product temperature of 30° C.
Result:
Yield: 890 g flowable product
Sieve analysis: 94%<500μ
Bulk weight: 616 g/l

EXAMPLE 2

Fluid-bed drying system Glatt company GPCG 1 / Topspray with two-component [two-fluid, binary] nozzle d=1.2 mm; nozzle installation "top"; spray pressure: 1.4 bar
Initial product: 250 g thioctic acid (sieved<1250μ)
Spray solution: 750 g thioctic acid, 1125 g acetone The initial product is heated to 20° C. with the aid of the supply air approximately 30° C. warm and the spraying in of the solution is started at this product temperature. Spray rate: 38 g/min, during which the dosing is gradually raised to 61 g/min. The supply-air temperature is maintained constant at 30° C. The product temperature settles [is adjusted] to 19°–22° C.

After the end of the spraying [in] the matter is allowed to dry 10 min at a product temperature of 30° C.
Result:
Yield: 910 g flowable product
Sieve analysis: 99%<500μ
Bulk weight: 680 g/l

EXAMPLE 3

Fluid-bed drying system Glatt company GPCG 1 / Topspray with two-component [two-fluid, binary] nozzle d=1.2 mm; nozzle installation "top"; spray pressure: 1.4 bar
Initial product: 250 g thioctic acid (sieved <1250μ)
Spray solution: 750 g thioctic acid, 1125 g acetone The initial product is heated to 30° C. with the aid of the supply air approximately 40° C. warm and the spraying in of the solution is started at this product temperature. Spray rate: 25 g/min, during which the dosing is gradually raised to 59 g/min. The supply-air temperature is maintained constant at 40° C. The product temperature settles [is adjusted] to 28°–32° C.

After the end of the spraying [in] the matter is allowed to dry 10 min at a product temperature of 30° C.
Result:
Yield: 970 g flowable product
Sieve analysis: 99%<500μ
Bulk weight: 690 g/l

EXAMPLE 4

Fluid-bed drying system Glatt company GPCG 1 / Topspray with two-component [two-fluid, binary] nozzle d=1.2 mm; nozzle installation "top"; spray pressure: 1.4 bar
Initial product: 250 g thioctic acid (sieved<1250μ)
Spray solution: 750 g thioctic acid, 1125 g ethyl acetate The initial product is heated to 20° C. with the aid of the supply air approximately 30° C. warm and the spraying in of the solution is started at this product temperature. Spray rate: 40 g/min, during which the dosing is gradually raised to 65 g/min. The supply-air temperature is maintained constant at 30° C. The product temperature settles [is adjusted] to 19°–23° C.

After the end of the spraying [in] the matter is allowed to dry 10 min at a product temperature of 30° C.
Result:
Yield: 920 g flowable product
Sieve analysis: 99%<500μ
Bulk weight: 686 g/l

EXAMPLE 5

Fluid-bed drying system Glatt company GPCG 1 / Topspray with two-component [two-fluid, binary] nozzle d=1.2 mm; nozzle installation "top"; spray pressure: 1.4 bar
Initial product: 250 g thioctic acid (sieved<1250μ)
Spray solution: 750 g thioctic acid, 1125 g ethanol The initial product is heated to 20° C. with the aid of the supply air approximately 30° C. warm and the spraying in of the solution is started at this product temperature. Spray rate: 43 g/min, during which the dosing is gradually raised to 64 g/min. The supply-air temperature is maintained constant at 30° C. The product temperature settles [is adjusted] to 20°–23° c.

After the end of the spraying [in] the matter is allowed to dry 10 min at a product temperature of 30° C.
Result:
Yield: 912 g flowable product
Sieve analysis: 98%<500μ
Bulk weight: 680 g/l For examples 6 and 7 dry thioctic acid with the following residual solvent contents was used:
Cyclohexane: 3200 ppm
Ethyl acetate: 1900 ppm

EXAMPLE 6

Fluid-bed drying system Glatt company GPCG 15 / Topspray with circulatory gas distribution; two-component [two-fluid, binary] nozzle d=2.2 mm; nozzle installation "top"; spray pressure: 1.8 bar
Initial product: 4 kg thioctic acid (granulated matter)
Spray solution: 16.8 kg thioctic acid, 25 kg acetone
Air amount (fluid bed): 400–550 m$^3$/h The initial product is heated to 20° C. with the aid of the supply air approximately 30° C. warm and the spraying in of the solution is started at this product temperature. Spray rate: 330 g/min, during which the dosing is gradually raised to 620 g/min. The supply-air temperature is maintained constant at 30° C. The product temperature settles [is adjusted] to 16°–18° C.

After the end of the spraying [in] the matter is allowed to dry 10 min at a product temperature of 30° C.

| Result: | |
|---|---|
| Yield: | 19.9 kg flowable product |
| Content: | 98.3% by weight |
| Polymer content: | <2% by weight |
| Sieve analysis: | 1% > 1000μ |
|  | 11% > 710μ |
|  | 70% > 500μ |
|  | 9% > 335μ |
|  | 8% > 250μ |
|  | 1% > 100μ |
| Bulk weight: | 770 g/l |
| Residual-solvent content: | |
| Cyclohexane: | 104 ppm |
| Ethyl acetate: | 22 ppm |
| Acetone: | 345 ppm |

EXAMPLE 7

Fluid-bed drying system Glatt company GPCG 15 / Topspray with circulatory gas distribution; two-component

[two-fluid, binary] nozzle d=2.2 mm; nozzle installation "middle"; spray pressure: 1.2–1.5 bar
Initial product: 4 kg thioctic acid (sieved matter)
Spray solution: 16.8 kg thioctic acid, 25 kg acetone
Air amount (fluid bed): 390–600 m³/h The initial product is heated to 20° C. with the aid of the supply air approximately 30° C. warm and the spraying in of the solution is started at this product temperature. Spray rate: 386 g/min, during which the dosing is gradually raised to 470 g/min. The supply-air temperature is maintained constant at 30° C. The product temperature settles [is adjusted] to 19°–20° C.

After the end of the spraying [in] the matter is allowed to dry 10 min at a product temperature of 30° C.

| Result: | |
|---|---|
| Yield: | 19.3 kg flowable product |
| Content: | 98.5% by weight |
| Polymer content: | <2% by weight |
| Sieve analysis: | 3% > 1000μ |
| | 5.1% > 710μ |
| | 53% > 500μ |
| | 37.5% > 250μ |
| | 0.5% > 100μ |
| Bulk weight: | 728 g/l |
| Residual-solvent content: | |
| Cyclohexane: | 576 ppm |
| Ethyl acetate: | 151 ppm |
| Acetone: | 257 ppm |

EXAMPLE 8

Fluid-bed drying system Glatt company GPCG 15 / Topspray with circulatory gas distribution; two-component [two-fluid, binary] nozzle d=2.2 mm; nozzle installation "middle"; spray pressure: 2 bar
Initial product: 4 kg thioctic acid (moist product)
Spray solution: 10 kg thioctic acid, 18 kg ethyl acetate
Air amount (fluid bed): 550 M³/h The initial product is heated to 26° C. with the aid of the supply air approximately 30° C. warm and predried at this product temperature. The spraying in of the solution is then started. Spray rate: 240 g/min, during which the dosing is gradually raised to 500 g/min. The supply-air temperature is maintained constant at 30° C. The product temperature settles [is adjusted] to 19°–24° C.

After the end of the spraying [in] the matter is allowed to dry 10 min at a product temperature of 35° C.

| Result: | |
|---|---|
| Yield: | 11.5 g flowable product |
| Content: | 99.6% by weight |
| Polymer content: | <1% by weight |
| Sieve analysis: | 0.10% > 2000μ |
| | 0.40% > 1400μ |
| | 0.90% > 1000μ |
| | 2.19% > 710μ |
| | 4.78% > 500μ |
| | 6.39% > 355μ |
| | 33.3% > 250μ |
| | 45.56% > 180μ |
| | 6.18% > 125μ |
| | 0.20% > 90μ |
| | 0.0% > 63μ |

EXAMPLE 9

Tests were carried out to determine the specific surface and pore distribution in order to further specify and describe the product of the invention.

The following thioctic-acid products were tested:
Sample 1 (commercially available specimen)
Sample 2 (commercially available specimen)
Sample 3 (product used for examples 6–8)
Sample 4 (product in accordance with the invention resulting from example 6)
Sample 5 (product in accordance with the invention resulting from example 7)
Sample 6 (product in accordance with the invention resulting from example 8)

The following determinations were carried out:
1. Determination of the specific surface according to the carrier-gas method (single-point method):

The method is described in principle (without detailed method parameters) in DIN 66131, par. 4.3.4).

This specification is described in detail in ASTM D 4567-86 ("Standard Test Method for Single-Point Determination of Specific Surface Area of Catalysts Using Nitrogen Adsorption by Continuous flow Method"). Deviating from this specification, the degassing was carried out in the nitrogen current at room temperature.

The determination of the mesopore volume and mesopore distribution took place with the equipment software of ASAP 2400 (Micromeritics company) from the statically and volumetrically measured sorption isotherm of nitrogen at T=77K (see DIN 66131): The mesopore volume is obtained by converting the gas volume absorbed at $p/p_0$=0.931 (corresponds to a pore diameter of approximately 30 nm) to condensate volume, taking the micropore volume into consideration, if necessary. The mesopore distribution is calculated according to the method of Barett, Joyner and Halenda (ASTM D 4641–88) from the sorption isotherm. This method is described in DIN 66134 (8th presentation of standard). The pretreatment of the sample took place at room temperature under a vacuum.

| Result: | | | |
|---|---|---|---|
| Determination | Sample 1 | Sample 2 | Sample 3 |
| Spec. surface (m²/g) | 0.60/0.61 | 0.22/0.25 | 0.59/0.68 |
| Micropores: D < 2 nm | none present | none present | none present |
| Mesopores: d = 2–30 nm (ml/g) | none present | none present | none present |
| Macropores D > 30 nm | 1.06 | 0.79 | 0.96 |
| Determination | Sample 4 | Sample 5 | Sample 6 |
| Spec. surface (m²/g) | 0.97/1.01 | 0.87/0.87 | 0.84/0.89 |
| Micropores: D < 2 nm | none present | none present | none present |
| Mesopores: d = 2–30 nm (ml/g) | 0.004 | 0.003 | 0.003 |
| Macropores D > 30 nm | 0.42 | 0.36 | 0.52 |

Primarily grain interstices were measured here in the macropore range.

What is claimed:
1. A method of producing flowable R,S-thioctic acid which can be further processed galenically by pressing to highly concentrated solid presentations with contents of more than 200 mg pure thioctic acid, said method comprising the steps of placing a stationary phase of thioctic acid in a fluid bed, and spraying a solution of thioctic acid onto the thioctic acid placed in the fluid bed while simultaneously removing solvent; to obtain a flowable granulate of thioctic acid.

2. The method according to claim 1, wherein said stationary phase is solvent-moist thioctic acid.

3. The method according to claim 1 or 2, wherein said stationary phase is more than 10% by weight and less than 50% by weight relative to the total weight dry thioctic acid, said total weight being the sum of the stationary phase and sprayed-on thioctic acid.

4. The method according to claim 3, wherein said stationary phase is approximately 25% by weight relative to the total weight dry thioctic acid.

5. The method according to claim 2, wherein the solvent-moist thioctic acid has been prepared by dissolving one part thioctic acid at 10° C. to 60° C. in 5–20 parts solvent or solvent mixture and cooling said mixture within 2 to 10 hours to 0° C. to −20° C., said solvent or solvent mixture having a relative permittivity $\epsilon$ between 2.5 and 5.5.

6. The method according to claim 1 or 2, wherein a highly-concentrated solution of thioctic acid is sprayed onto the stationary phase while adjusting product temperature, spray pressure and spray rate so that solvent evaporates and thioctic acid crystallizes out.

7. The method according to claim 6, wherein the solution of thioctic acid is sprayed into the fluid bed with a temperature in a range of 0° to 60° C.

8. The method according to claim 6, wherein spraying is carried out at 100 to 1200 mbar.

9. The method according to claim 1 or 2, wherein the solution of thioctic acid comprises aromatic, aliphatic or cycloaliphatic, organic solvents.

10. The method according to claim 9 wherein the solution of thioctic acid comprises acetone or ethyl acetate.

11. The method according to claim 9, wherein the concentration of the solution of thioctic acid is between 10 and 80%.

12. The method according to claim 1, wherein a flowable product with a bulk weight between 500 and 900 g/l is obtained which has a grain-size distribution and particle quality suitable for being galenically further processed to solid presentations or for being pressed into highly-concentrated, solid presentations.

13. The method according to claim 1 wherein a product is obtained with a residual solvent content of organic solvents of <1000 ppm.

14. A composition of R,S-thioctic acid which has a specific surface of >0.7 $m_2$/g and a number of mesopores with a diameter between 2 and 30 nm.

15. The composition according to claim 14, wherein the volume of the mesopores with a diameter between 2 and 30 nm is between 0.001 and 0.005 ml/g per gram R,S-thioctic acid.

16. The composition of claim 14 or 15, wherein the ratio of the volume of mesopores with a diameter between 2 and 30 nm per gram R,S-thioctic acid to the volume of macropores with a diameter >30 nm per gram R,S-thioctic acid is between 1:1000 and 1:10.

17. The composition of claim 16, wherein the ratio is between 1:200 and 1:50.

18. A medicament which is produced by the method of claim 1 or 2.

19. A medicament comprising the composition of claim 14.

* * * * *